(12) United States Patent
Rein et al.

(10) Patent No.: US 7,235,048 B2
(45) Date of Patent: Jun. 26, 2007

(54) DEVICE FOR RETRACTING TISSUE

(75) Inventors: Joachim Rein, Korntal (DE); Wolfgang Hemmer, Wernau (DE); Thomas F. Kupka, Auenwald (DE); Walter Rehm, Korntal (DE)

(73) Assignee: Max Hauser Süddeutsche Chirurgie-Mechanik GmbH, Tuttlingen (DE)

( * ) Notice: Subject to any disclaimer, the term of this patent is extended or adjusted under 35 U.S.C. 154(b) by 0 days.

(21) Appl. No.: 10/831,373

(22) Filed: Apr. 26, 2004

(65) Prior Publication Data

US 2005/0020885 A1 Jan. 27, 2005

(30) Foreign Application Priority Data

Apr. 29, 2003 (DE) ................. 103 19 430

(51) Int. Cl.
*A61B 1/32* (2006.01)
(52) U.S. Cl. .................................... 600/228
(58) Field of Classification Search ............... 600/201, 600/203, 210, 215–16, 221, 225, 228
See application file for complete search history.

(56) References Cited

U.S. PATENT DOCUMENTS

| | | | | | |
|---|---|---|---|---|---|
| 4,143,652 | A | * | 3/1979 | Meier et al. | 600/203 |
| 4,949,707 | A | * | 8/1990 | LeVahn et al. | 600/234 |
| 5,057,423 | A | * | 10/1991 | Hiserodt et al. | 435/5 |
| 5,846,194 | A | * | 12/1998 | Wasson et al. | 600/228 |
| 5,944,736 | A | * | 8/1999 | Taylor et al. | 606/198 |
| 5,976,080 | A | * | 11/1999 | Farascioni | 600/213 |
| 6,113,535 | A | * | 9/2000 | Fox et al. | 600/228 |
| 6,132,370 | A | * | 10/2000 | Furnish et al. | 600/235 |
| 6,231,506 | B1 | * | 5/2001 | Hu et al. | 600/210 |
| 6,254,532 | B1 | | 7/2001 | Paolitto et al. | |
| 6,315,718 | B1 | * | 11/2001 | Sharratt | 600/228 |
| 2002/0077532 | A1 | | 6/2002 | Gannoe et al. | |

* cited by examiner

*Primary Examiner*—Eduardo C. Robert
*Assistant Examiner*—Annette Reimers
(74) *Attorney, Agent, or Firm*—The Nath Law Group; Jerald L. Meyer; Teresa M. Arroyo

(57) ABSTRACT

A device (1) for retracting tissue with a retaining element (2) with a throughgoing cutout (7) and with a blade (18) mounted on a retractor arm (16), retractor arm (16) being seated movably in cutout (7), wherein cutout (7) of retaining element (2) is formed in a groove shape.

38 Claims, 7 Drawing Sheets

DEVICE FOR RETRACTING TISSUE

FIELD OF THE INVENTION

The present invention pertains to a device for retracting tissue and other parts of the body during surgical interventions according to the preamble of Claim 1.

BACKGROUND OF THE INVENTION

A device of this class for retracting tissue comprises as a rule a retaining element with a throughgoing cutout, as well as a blade fastened on a retractor arm. In this case, the rod is seated movably in the cutout of the retaining element and can be fixed in place by means of a locking element in a desired position on the retaining element.

DE 199 23 534 C1 discloses a retractor unit with several blades, each arranged on a retractor arm. The retractor arms are arranged along a straight rod so as to be movable and lockable thereon. Each retractor arm is connected to the rod via a connecting element referred to as a rack box, said rack box comprising two hole-like cutouts running perpendicular to one another and extending through the rack box. The rod is guided movably and lockably in one of the hole-like cutouts and the retractor arm is guided movably and lockably in the other of the cutouts. The retractor arm is linked to the rack box by introducing the retractor arm in the area of its free axial end into the hole-like cutout of the rack box.

In the retraction of the tissue, the blade is hooked into the tissue to be retracted and the refraction position is determined by displacing the retractor arm along and perpendicular to the rod by means of the rack box. This has the disadvantage that the adjustment of the desired retraction position of the tissue to be retracted is often cumbersome and is done with too little feeling.

There has therefore long been a need to provide a retracting device that makes it possible for the surgeon to retract the sensitive tissue that is to be retracted with feeling by hand by means of the blades and then to insert the blades into the retracting device in the desired retraction position of the tissue.

SUMMARY OF THE INVENTION

The present invention is therefore based on the problem of proposing a device for retracting tissue in which blades can be inserted into the retracting device simply and with maintenance of the desired retraction position of the tissue.

This problem is solved according to the invention by a device for retracting tissue with the characteristics of Claim 1.

The device according to the invention for retracting tissue comprises a retaining element with throughgoing cutout, as well as a blade held in place on a retractor arm, the retractor arm being movably seated in the cutout.

In the device according to the invention for retracting tissue, it is also provided that the cutout is formed in the shape of a groove.

By virtue of the invention it is possible to insert the retractor arm into the cutout of the retaining element from above due to its groove-like construction. Thus, a retractor arm need not be inserted in the area of its free axial end into the hole-like cutout of the retaining element, as in devices for retracting tissue known from the prior art. With the device according to the invention for retracting tissue, it is thus easy for a surgeon to retract the sensitive tissue that is to be retract by means of the blade in a first step and then to fix this blade in the desired retracting position by insertion of the retractor arm into the groove-shaped cutout of the retaining element. A simple and sensitive handling of the blades when retracting the tissue is thereby possible.

For the retracting devices known from prior art, the retraction position of the blades can be adjusted as a rule with four degrees of freedom, in either a graduated or a continuous manner. For some retracting devices, the degrees of freedom are defined by three axes of rotation and by longitudinal movability of the retractor arm or blade along one of the axes of rotation. In these known retracting devices there is, of course, the disadvantage that the retraction position of the blades in the individual degrees of freedom cannot be set independently of the other degrees of freedom. In concrete terms, this means, for instance, that by setting the second degree of freedom when the first degree of freedom has been set, the position of the blade in the first degree of freedom is also influenced, so that the adjustment of the blades to achieve a desired retraction position is often time-consuming and cumbersome for the surgeon.

The basis of the present invention is therefore the problem of proposing a device for retracting tissue in which the blades can be easily adjusted to achieve the desired retraction position of the tissue, and in which the individual degrees of freedom do not influence one another.

This problem is solved according to the invention by a device for retracting tissue with the characteristics of Claim 2. The device of this class for retracting tissue has a slide part and a retractor arm on which a blade is mounted. The retractor arm is in this case seated on the slide part and can be moved relative to the slide part with at least four degrees of freedom, at least four degrees of freedom being defined by at least three axes.

The device according to the invention for retracting tissue is characterized in that at least three axes intersect in at least one point.

By virtue of the invention, therefore, a device for retracting tissue is created, with which each of the four degrees of freedom of the blades can be adjusted independently. Because of the characteristic of the invention that at least three axes intersect in at least one point, there is no change in the blade position of any other degree of freedom when one degree of freedom is adjusted, which would be the case if the three axes defining the four degrees of freedom did not intersect in at least one point. Thus, a device for retracting tissue with which the position of the blades in the four degrees of freedom is easily adjustable is created by the invention. It should further be noted at this point that it is also possible that, in a given position, on of the axes can coincide with another of the axes (for example, if the longitudinal axis 17 of FIG. 3 is pivoted vertically upwards.

Preferred embodiments and advantageous refinements are specified in the subordinate claims.

It is of course possible to create a device for retracting tissue that comprises the characteristics of Claim 1 as well as the characteristics of Claim 2.

In order to design the handling of the device for retracting tissue to be particularly simple, so that the blade position can be easily fixed and easily released, a particularly preferred embodiment provides a clamping wheel that can be brought from a first position, in which the retractor arm is movable relative to the slide part, into a second position, in which the retractor arm is fixed relative to the slide part in all degrees of freedom. With this embodiment it is consequently possible for the surgeon, by means of a single actuating element, namely, a clamping wheel, to fix the desired position of the blade after adjustment has been accomplished, or to release it again when the position is to be changed. One-handed manipulation of the device for retracting tissue in fixing or releasing or releasing the blade position is thus possible by means of this embodiment, so that the surgeon can hold the blade fastened to the retractor arm in the desired retraction position of the tissue, and can fix the blade in it with the other hand via the clamping wheel.

There are various possibilities for implementing the four degrees of freedom of the blades relative to the slide part. A preferred embodiment provides that a first degree of freedom is created by infinitely variable rotatability about a first axis of rotation, a second degree of freedom by infinitely variable rotatability about a second axis of rotation, a third degree of freedom by infinitely variable rotatability about a third axis of rotation and fourth degree of freedom by infinitely variable movability along the third axis. Thus the blade position can be adjusted with infinite variability in any arbitrary direction in space. In this regard, it usually makes sense if the axes of rotation that are not simultaneously axes of displacement run mutually perpendicular.

An additional preferred embodiment provides that the retractor arm can be displaced along its longitudinal axis in the cutout of the retaining element. Moreover, a particularly preferred embodiment provides that the retractor arm can be rotated about its longitudinal axis in the cutout of the retaining element. By virtue of the guidance of the retractor arm in the cutout of the retaining element, two degrees of freedom, namely, the above-referenced third degree of freedom by infinitely variable rotatability and the above-referenced fourth degree of freedom by infinitely variable movability.

There are various possibilities for realizing the two first degrees of freedom defined by the first and second axes of rotation. A particularly preferred embodiment of the invention provides that retaining element can be rotated relative to the slide element about the first and second axes of rotation.

A preferred embodiment of the invention provides that the retaining element has at least an approximately U- or V-shaped cross section. The retaining element formed in a U shape comprises two legs running essentially parallel to one another and joined together by a base plate. The retaining element formed in a V shape comprises two legs running at an angle to one another and intersecting. The groove-like cutout is formed for both types of cross section by the free area between the facing surfaces of the legs.

There are various possibilities for locking the retractor arm in the groove-like cutout of the retaining element. Thus it is possible, for instance, to provide on the retaining element a pin element projecting into the groove-like cutout, by means of which the retractor arm inserted into the cutout can be clamped in the cutout by the formation of a friction fit. It is conceivable in this regard for the pin element to be actively connected to a spring and to be pressed against the retractor arm by resilient deformation of the latter. Another possibility consists in providing screw threads on the pin element, with the retractor arm being clampable in the cutout by rotation of the pin element, creating a friction fit. A preferred embodiment provides that the retaining element comprises a clamping sleeve as well as a clamping part movably guided in the clamping sleeve, the cross section of the cutout being modifiable by displacement of the clamping part in the clamping sleeve. In other words, this implies that the retaining element comprises a clamping sleeve with a groove-like cutout, in which a clamping part with a groove-like cutout is movably guided. In this case, the cutout of the retaining element for holding the retractor arm is defined by the area of overlap of the cutout in the clamping sleeve and the cutout of the clamping part. The cross section of the cutout in the retaining element can be changed by relative displacement of clamping sleeve with respect to clamping part. Thus, a position can be defined in which the two cutouts completely overlap. In this position, the cutout of the retaining element has a maximal cross section. In this position, the retractor arm can be inserted into the cutout of the retaining element. If the clamping sleeve and the clamping part are displaced relative to one another, the cross section of the cutout of the retaining element changes, whereby the retractor arm is clamped or locked in place by formation of a friction fit on the retaining element.

There are various possibilities for realizing the relative movability of the clamping sleeve with respect to clamping part. A particularly preferred embodiment provides that the clamping part and the clamping sleeve can be displaced essentially parallel to the first axis of rotation.

In order to suppress the sliding out of the retractor arm from the groove-like cutout of the retaining element in an effective manner, a preferred embodiment of the invention provides a catch bead arranged on the clamping part and/or on the clamping sleeve and projecting into the groove-like cutout, so that the retractor arm is gripped circumferentially by an arc angle of more than 180° in the inserted state.

In many situations, there is a requirement placed on the device for retracting tissue that the retractor arm be insertable into the cutout of the retaining element with the aid of only one hand. It is advantageous for this requirement if the retaining element comprises means by which a catch or clip function is created, so that the retractor arm can be snapped or clipped into the cutout of the retaining element. In this context, the pin element already described above that projects into the cutout should be mentioned; it is actively connected to a spring such that the pin element is pressed against the retractor arm inserted into the cutout, whereby it is clamped in place in the cutout by the creation of a friction fit. If, as described above, the retaining element comprises a clamping sleeve and a clamping part, then a preferred embodiment of the invention provides a spring that is actively connected to the clamping sleeve and the clamping part such that the cross section of the cutout can be automatically reduced. This implies in other words that the maximal cross section of the cutout of the retaining element can be achieved only by resilient deformation of the spring and, when the spring is released, the clamping sleeve and the clamping part are displaced relative to one another by the restoring force of the spring, reducing the cross section of the cutout of the retaining element.

According to another particularly preferred embodiment, the clamping wheel is provided on the retaining element and is actively connected to the clamping part, the cross section of the cutout of the retaining element being reducible by actuation of the clamping wheel. Consequently, the clamping wheel can fix the two degrees of freedom of the blades in relation to the retaining element, which are defined by the retractor arm guided in the cutout of the retaining element, namely, by the rotatability of the retractor arm about its longitudinal axis in the cutout of the retaining element and the movability of the retractor arm along its longitudinal axis in the cutout of the retaining element.

Various possibilities of how the clamping part is actively connected to the clamping wheel are conceivable. A preferred embodiment of the invention provides that the clamping part comprises a rod-like section that is actively connected to the clamping wheel. One design based on this embodiment provides, for instance, that the rod-like section comprises screw threads and that the clamping wheel comprises a hole-like opening with interior screw threads complementary to these screw threads. Thus, the rod-like section of the clamping part can be screwed into the clamping wheel by relative rotation between clamping wheel and clamping part.

In order to be able to construct the retaining element in a particularly simple way, it makes sense if the rod-like section of the clamping part defines the first axis of rotation.

There are various possibilities for arranging the retaining element on the slide part. A particularly preferred embodiment of the invention provides that the retaining element is arranged on the slide part by means of a bearing block. In this case, the retaining element can be rotated about a first axis of rotation relative to the bearing block and the bearing block can be rotated relative to the slide part about the second axis of rotation. Thus, the first and second degrees of freedom of the blades relative to the slide part are realized by the introduction of a bearing block and the relative rotatability of the retaining element with respect to the bearing block and of the bearing block with respect to the slide part.

There are several possibilities for constructing the bearing block. A preferred embodiment of the invention provides that the bearing block comprises a base and a back wall extending essentially perpendicular to the base.

An additional preferred embodiment based on the above embodiment provides that the slide part and the bearing block are connected by means of a clamping screw arranged on the slide part, the free end of the clamping screw reaching through a cutout in the base of the bearing block and the free end being terminated by the head part. Consequently, the second axis of rotation is defined in this case by the clamping screw arranged on the slide part and penetrating through the cutout in the base of the bearing block.

There are various ways of realizing the embodiment of the invention, according to which the position of the retractor arm relative to the slide part can be fixed and again released by means of a clamping wheel for all degrees of freedom. A particularly preferred embodiment provides an angle element with a section arranged between the base and the head part. Here the first section can be moved relative to the base along a displacement path and comprises a contact surface facing the base, as well as a second contact surface comprising a head part and running along the displacement path at an angle to the first contact surface, so that by movement along the displacement path, the first section can be brought from a first position, in which the first section is not braced between the base and the head part, into a second position, in which the first section is braced between the base, and the head part and the bearing block is pressed against the slide part. Due to the fact that the bearing block is pressed against the slide part, the second degree of freedom of the blade relative to the slide part, defined by the second axis of rotation, is fixed in the desired position.

To guide the angle element along the displacement path between the first and the second position, a particularly preferred embodiment provides that the first section comprises a slot-like cutout extending in the displacement direction and bordered by the second contact surface. Thus, the clamping screw penetrates the cutout in the base of the bearing block as well as the slot-like cutout in the first section of the angle element, the first contact surface being braced against the base and the second contact surface being braced on the head part of the clamping screw by displacement of the angle element along the displacement path, so that as a result, the bearing block is braced against the head part of the clamping screw when the second position is reached, and thus afixing of the degree of freedom defined by the second axis of rotation is established.

A particularly preferred embodiment of the invention provides that the angle element can be displaced by means of the clamping wheel. Hence, the second degree of freedom defined by the second axis of rotation can be fixed by actuation of the clamping wheel.

A preferred embodiment of the invention provides that the degree of freedom defined by the first axis of rotation can be fixed by virtue of the fact that the angle element comprises a second section, the clamping part a contact area, and the clamping sleeve an additional contact area, the second section and the contact area being arranged between the back wall of the bearing block and the contact area of the clamping part and the two contact areas of the clamping part and clamping sleeve being adjacent to one another. Additionally, the rod-like section of the clamping part can be brought by displacement along a displacement path from a first position, in which the second section, the back wall and the two contact surfaces are not in contact with one another, into a second position, in which the second section, the back wall and the two contact surfaces are in contact with one another.

A preferred embodiment provides that the displacement path runs parallel to the first axis of rotation.

In order to construct the arrangement as simply as possible, an additional especially preferred embodiment provides that the second section, the contact area and the back wall each comprise a cutout, penetrated by the rod-like section of the clamping part.

To center the clamping sleeve and the clamping part during the fixing process, a particularly preferred embodiment provides that the contact area of the clamping part, the second section of the angle element and the contact area of the clamping sleeve are constructed, in the area where they can be brought into contact with one another, in an essentially complementary and, more particularly, conical form.

If the retaining element comprises the above-described clamping sleeve and the above-described clamping part, then a preferred embodiment based thereupon provides that the clamping sleeve is fastened on the bearing block so as to be pivotable about the first axis of rotation.

An additional, particularly preferred embodiment of the invention provides that the clamping sleeve comprises a slot running essentially parallel to the axis of rotation, in which a pin arranged on the clamping part is guided. By virtue of this characteristic of the invention, twisting of the clamping sleeve about the first axis of rotation relative to the clamping part is suppressed, so that the cross section of the cutout of the retaining element is not reduced by twisting of the clamping sleeve relative to the clamping part, which would have the result that the retractor arm could no longer be inserted into the cutout of the retaining element.

To limit the ability of the retaining element to twist about the first axis of rotation relative to the bearing block, a preferred embodiment provides that a pin that is actively connected to a slot in the retaining element is arranged on the bearing block, so that a rotational motion of the retaining element about the first axis of rotation relative to the bearing block is possible only within a given angular range. The handling ability of the retractor device according to the invention is considerably improved by this characteristic of the invention as well, since, in the unfixed state, it suppresses twisting of the retaining element into a position in which, for instance, the cutout is arranged such that insertion of the retractor rod would be impossible for the surgeon.

Another particularly preferred embodiment provides that the slide part can be displaced infinitely variably along a slide rod. This defines an additional degree of freedom for the blades because the slide part can be displaced relative to a slide rod.

In order to be able to lock the position of the retaining element, which is pivotable about the first axis of rotation and which comprises a clamping sleeve and a clamping part, in a given pivot position, an additional embodiment of the invention provides that the clamping part is movable relative to the bearing block and can be brought to rest against the bearing block.

BRIEF DESCRIPTION OF THE DRAWINGS

The invention will be further elucidated below using schematic drawings on the basis of preferred embodiments presented for the sake of example. Shown are.

DETAILED DESCRIPTION OF THE INVENTION

Figure 1:
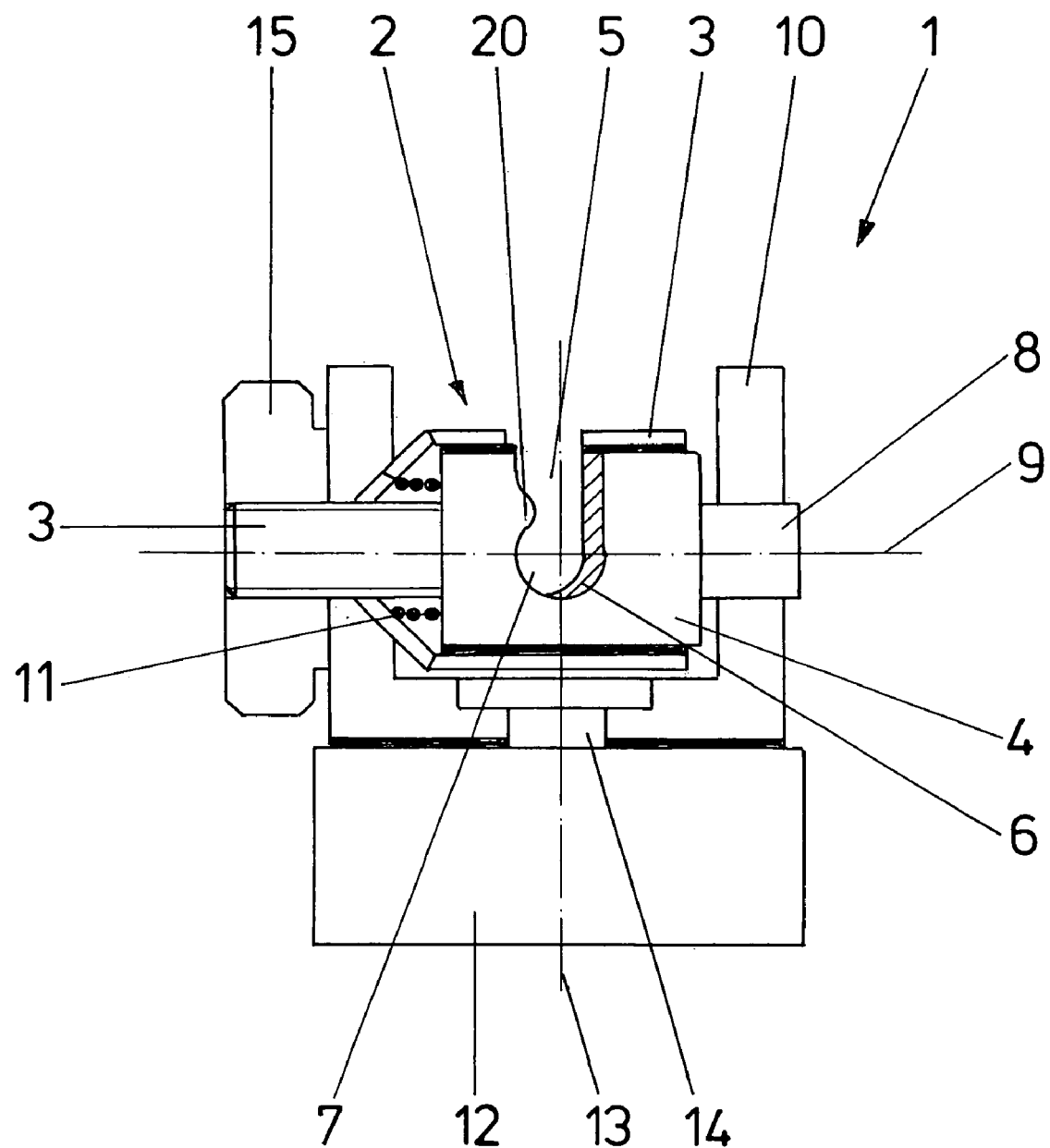
FIG. 1, a first embodiment of device according to the invention for retracting tissue in cross section, with the retractor arm of the blade not inserted.

FIG. 1 shows a device 1 according to the invention for retracting tissue in cross section with the retractor arm not inserted.

Device 1 for retracting tissue comprises a retaining element 2 with a clamping sleeve 3 and a clamping part 4 movably guided in clamping sleeve 3. Clamping sleeve 3 has a U-shaped cross section, by virtue of which a cutout 5 is formed in clamping sleeve 3 and a cutout 6 in clamping sleeve 4. In this case, each of the two cutouts 5 and 6 opens upwards in the representation of FIG. 1, the openings pointing in the same direction. Cutouts 5 and 6 extend continuously through clamping sleeve 3 and clamping part 4, respectively, so that a continuous cutout 7 of retaining element 2 with a groove shape is formed in the overlap area of the two cutouts 5 and 6. A retractor arm holding a blade in place can be inserted from above into groove-shaped cutout 7. A catch bead on clamping part 4 running in the direction of cutouts 5, 6 and 7 is provided to secure an inserted retractor arm (this matter is covered in greater detail in FIG. 2). In the current embodiment, clamping sleeve 3 is pivotably arranged about an axis of rotation 9 on a bearing block 10 by means of a shaft 8. A first axis of rotation 9 is thereby defined by shaft 8. Clamping part 4 can be displaced along first axis of rotation 9 relative to clamping sleeve 3 and bearing block 10. By displacing clamping part 4 in relation to clamping sleeve 3, the overlap area of the two cutouts 5 and 6 of the clamping sleeve and the clamping part 4, respectively, and thus the cross section of groove-like cutout 7 of retaining element 2, can be modified. A spring 11 is braced between clamping sleeve 3 and clamping part 4. Spring 11, clamping sleeve 3 and clamping part 4 are matched to one another such that, in a state in which no retractor arm is inserted into groove-like cutout 7, said groove-like cutout 7 has a smaller cross section than the retractor arm in the area in which the reactor arm is to make contact. This situation is shown in FIG. 1, Bearing block 10 is mounted on a slide part 12 so as to be able to pivot about a second axis of rotation 13. Said second axis of rotation 13 is defined by a shaft 14 connecting bearing block 10 and slide part 12. A clamping wheel 15 in active connection with clamping part 4 is also provided, whereby the cross section of cutout 7 can likewise be modified by relative motion of clamping sleeve 3 and clamping part 4. Furthermore, clamping part 4 can be put into contact with the bearing block at the right in FIG. 1 by rotation of clamping wheel 15, whereby the pivot position of the retractor arm about first axis of rotation 9 can be fixed.

Figure 2:
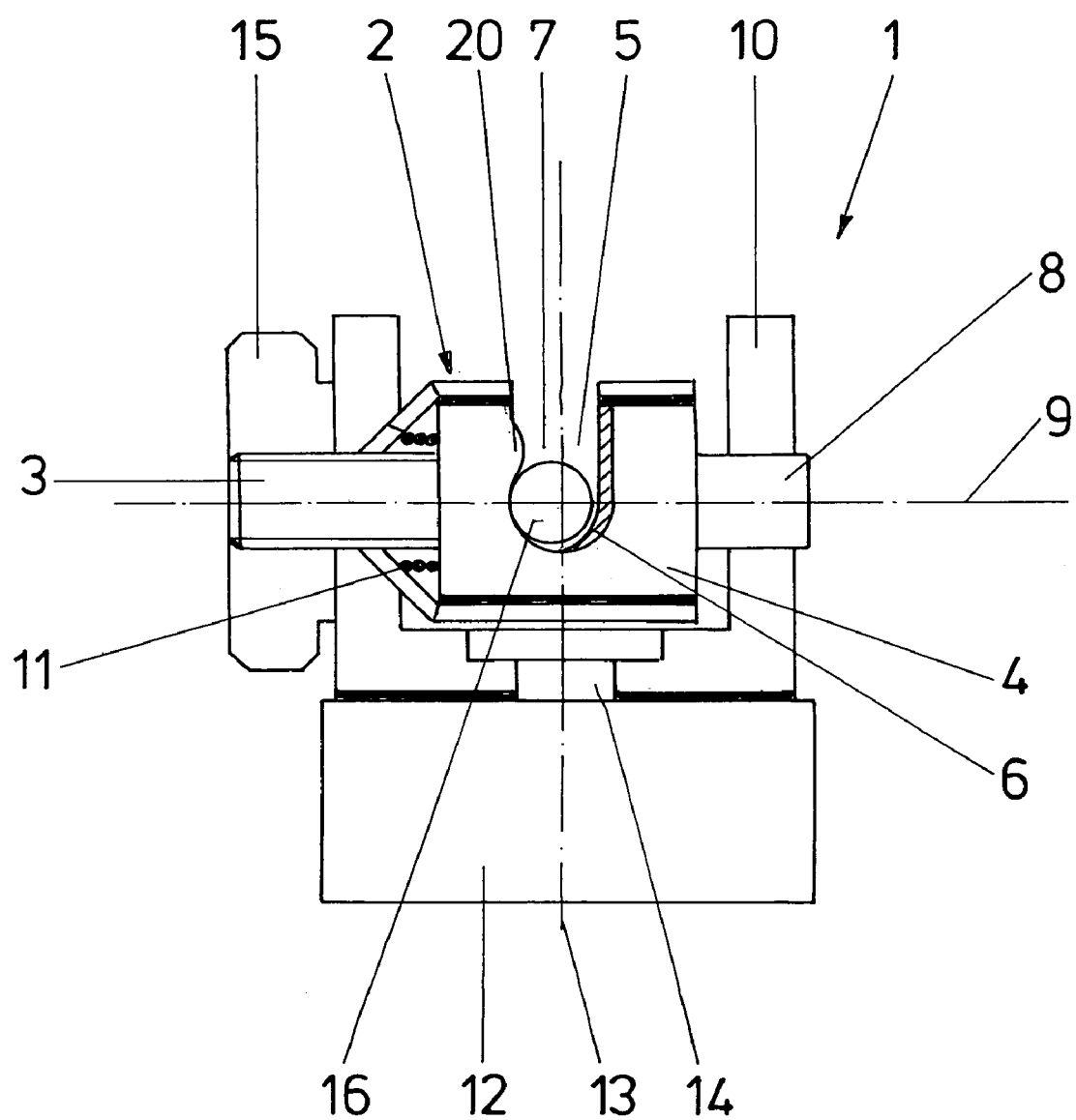
FIG. 2, the device according to the invention of FIG. 1 with the retractor arm of the blade inserted.

FIG. 2 shows the device according to the invention 1 of FIG. 1 with a retractor arm 16 inserted into groove-like cutout 7. A clip or catch function is provided by clamping part 4 movably guided with respect to clamping sleeve 3 and by spring 11 braced between clamping part 4 and clamping sleeve 3. As already described in FIG. 1, retractor arm 16 can be inserted from above into groove-like cutout 7 of retaining element 2. During insertion of retractor arm 16, clamping part 4 is shifted under initial tension from spring 11 until groove-like cutout 7 formed by cutouts 6 and 5 has a cross section that is at least as large as the cross section of retractor arm 16. When retractor arm 16 has been inserted down to the bottom of groove-like cutout 7, clamping part 4 is shifted back by the elastic restoring force of spring 11 (to the right in FIG. 2) until retractor arm 16 is clamped in place in groove-like cutout 7 between clamping sleeve 3 and clamping part 4 by the formation of a friction fit. Catch bead 20 has the effect that retractor arm 16 is gripped circumferentially by more than 180° by retaining element 2 formed by clamping sleeve 3 and clamping part 4. In the inserted state of retractor arm 16, a longitudinal axis, along which retractor arm is movably seated in cutout 7 of retaining element 2, is defined in the midpoint of the cross section of retractor arm 16. Retractor arm 16 is fixed in its longitudinal movement with respect to retaining element 2 by the clamping action between the two cutouts 5 and 6 of clamping sleeve 3 and clamping part 4. In the present embodiment, first axis of rotation 9, second axis of rotation 13 and longitudinal axis 17 intersect one another.

Figure 3:
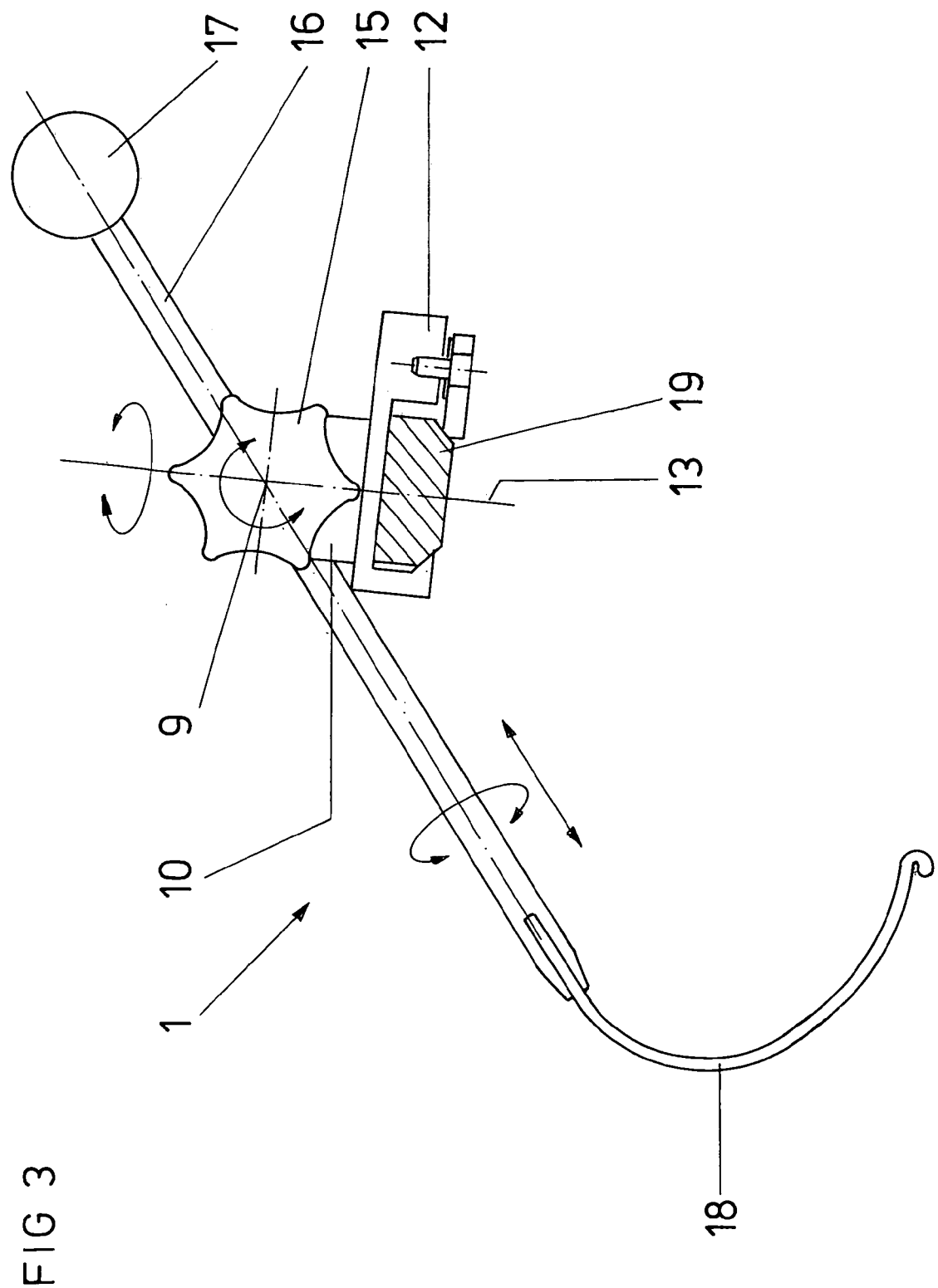
FIG. 3, the device according to the invention with inserted the retractor arm of the blade in a plan view.

FIG. 3 shows device according to the invention 1 in a side view. FIG. 3 shows retaining element 2 with bearing block 10 and retractor arm 16, on which a blade 18 is mounted. As is recognizable in FIG. 3, retractor arm 16, mounted in cutout 7 (not shown) of retaining element 2, can be pivoted about first axis of rotation 9 pointing vertically out of the drawing plane of FIG. 3. The first degree of freedom of retractor arm 16 relative to slide part 12 is defined by the first axis of rotation. Bearing block 10 is mounted on slide part 12 so as to pivot about second axis of rotation 13. The second degree of freedom of retractor rod 16 relative to slide part 12 is defined by the second axis of rotation.

First axis of rotation 9 and second axis of rotation 13 intersect at right angles.

Additionally, the third and fourth degrees of freedom are defined by longitudinal axis 17 of retractor rod 16, the third degree of freedom being described by the rotatability of retractor arm 16 about longitudinal axis 17 and the fourth degree of freedom by movability along longitudinal axis 17.

As is recognizable in FIG. 3, axes of rotation 9, 13 and 17 intersect at precisely one point. If retractor arm 16 were pivoted vertically upwards about first axis of rotation 9, then the two axes of rotation 17 and 13 would coincide. In this case, rotary axes 17 and 13 would intersect at infinitely many points. Furthermore, axis of rotation 9 would intersect the two axes of rotation 17 and 13 at precisely one point.

Also provided is a slide rod 19 on which in turn slide part 12 is seated so as to be able to move along an axis perpendicular to the plane of the drawing of FIG. 3.

Figure 4:
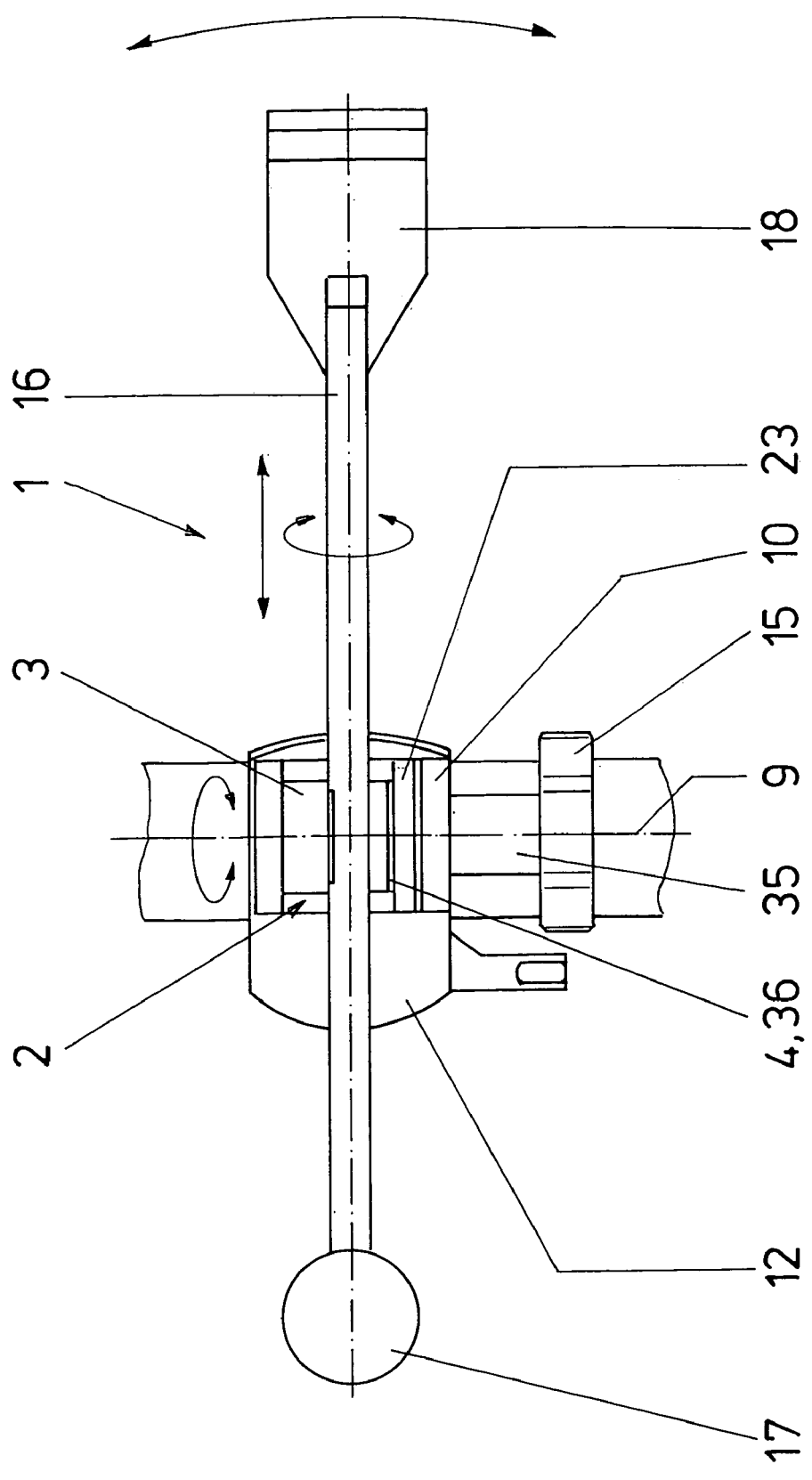
FIG. 4, the device according to the invention with inserted the retractor arm of the blade in the longitudinal direction.

FIG. 4 shows a device according to the invention 1 for retracting tissue in a plan view. In FIG. 4, second axis of rotation 13, about which bearing block 10 can pivot relative to slide part 12, in perpendicular to the plane of the drawing. In groove-like cutout 7 of retaining element 2 comprising clamping sleeve 3 and clamping part 4, retractor arm 16 is seated so as to be able to move along longitudinal axis 17. As already described in FIG. 2, retractor arm 16 is clamped in place in groove-like cutout 7 by a friction fit due to the elastic restoring force of spring 11, which is braced between clamping sleeve 3 and clamping part 4.

Figure 5A:
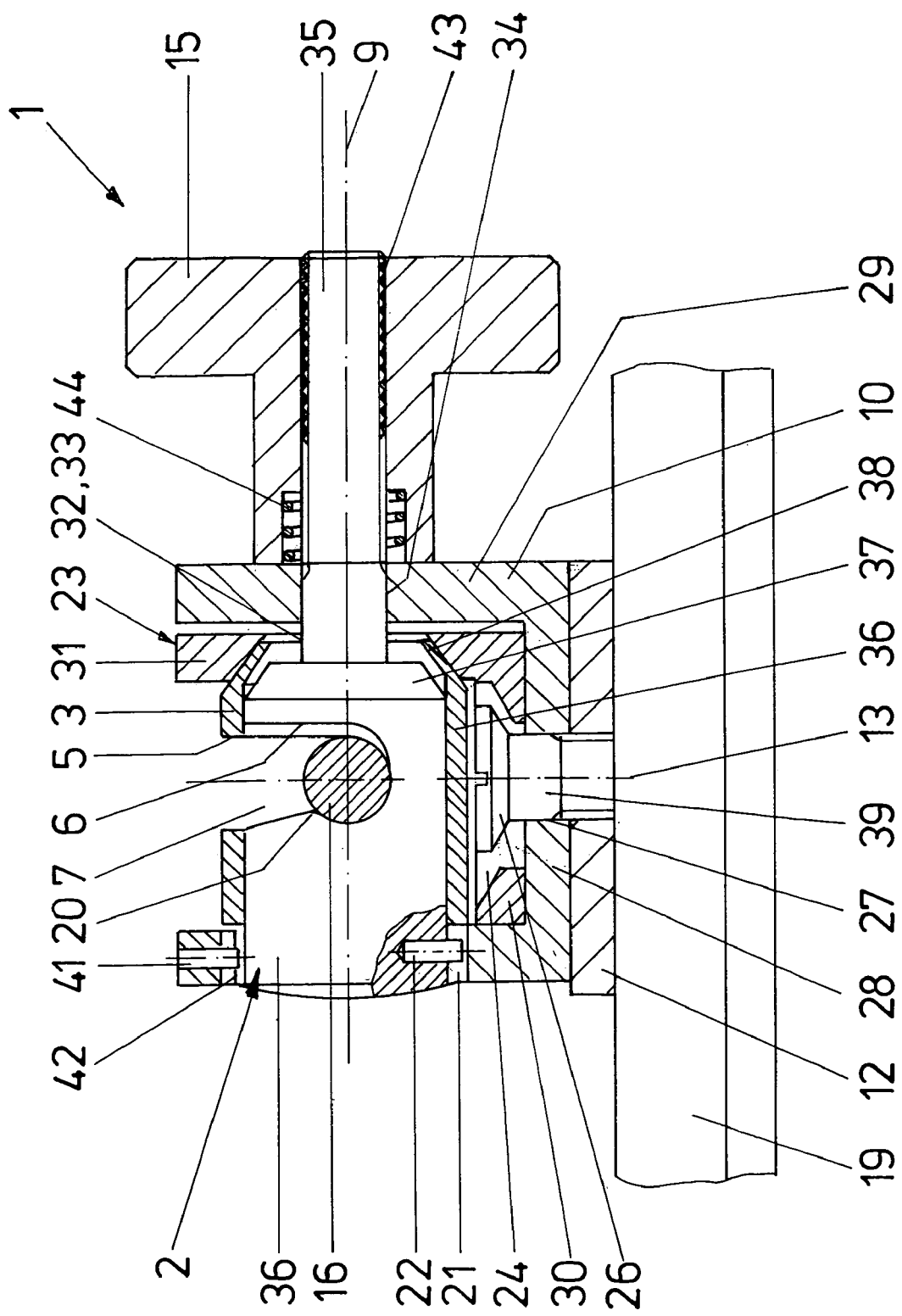
FIG. 5, a second embodiment of a device according to the invention for retracting tissue with the inserted or partially inserted retractor arm in cross section.
Figure 5B:
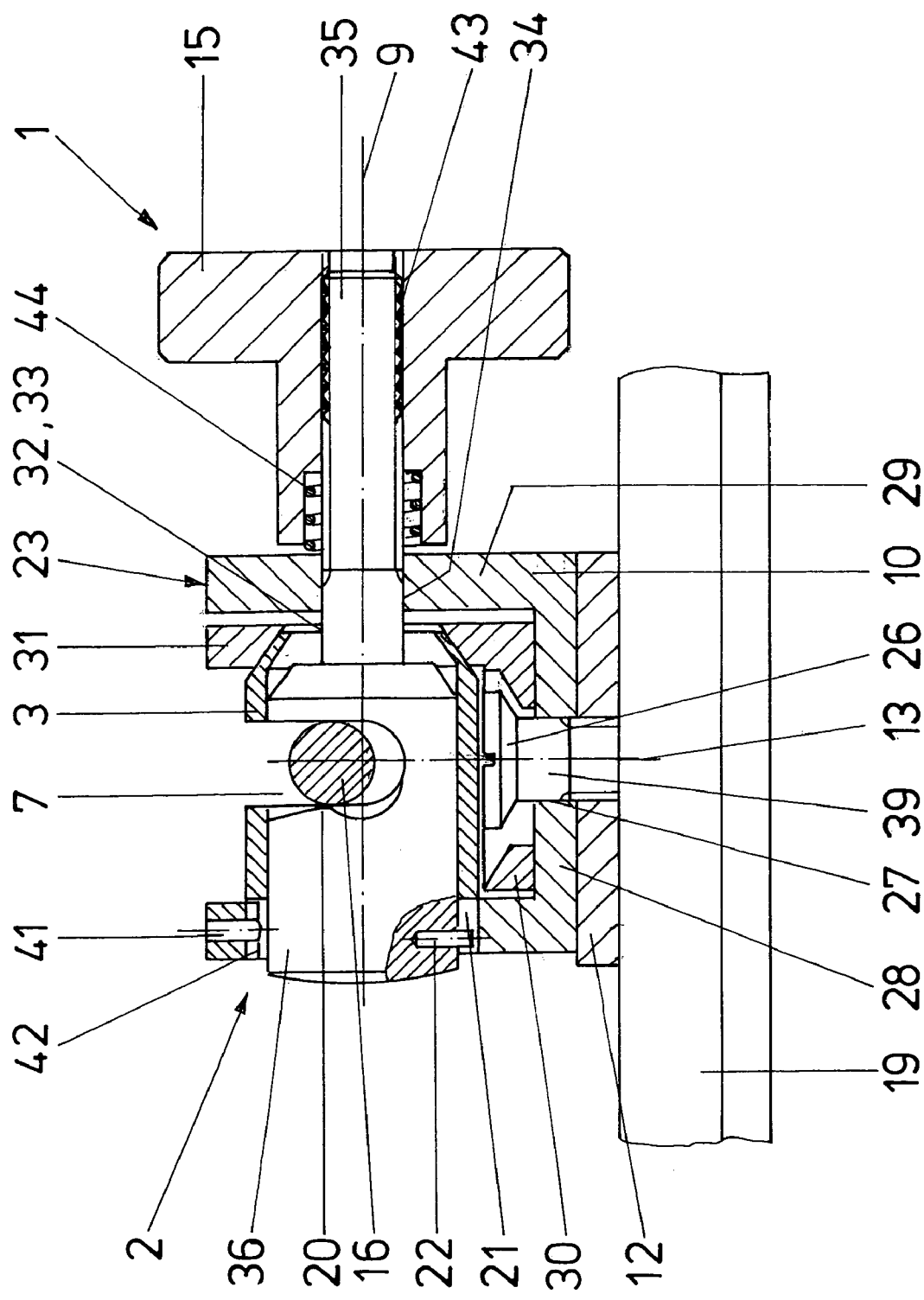

FIG. 5 shows a second embodiment of device according to the invention 1 for retracting tissue is cross section. In the discussion of FIGS. 5a and 5b, the differences from the first embodiment shown in FIGS. 1 and 2 will be the major focus.

FIG. 5a shows a device according to the invention 1 with inserted retractor arm 16 in a position in which all degrees of freedom of retractor arm 16 are fixed in place relative to slide part 12. Device 1 comprises a retaining element 2 with cutout 7. Retaining element 2 further comprises a clamping sleeve 3 and a clamping part 36. Clamping part 36 comprises a rod-like section 35. Clamping part 36 and clamping sleeve 3 can be displaced relative to one another along an axis of displacement. The axis of displacement simultaneously constitutes a first axis of rotation 9. Retaining element 2 is seated in a bearing block 10. Retaining element 2 can be rotated relative to bearing block 10 about the first axis of rotation. Clamping sleeve 3 comprises a slot 21 running parallel to first axis of rotation 9. A pin 22 arranged on clamping part 36 is guided in slot 21. A relative twisting between clamping sleeve 3 and clamping part 36 about the first axis of rotation is suppressed by the active connection between slot 21 and pin 22. Bearing block 10 comprises a pin 41, shown on the right side in FIG. 5, that engages in a slot 42 provided on retaining element 2. Slot 42 runs essentially parallel to axis of rotation 9 defining the displacement direction. A maximum angle of rotation of retaining element 2 relative to bearing block 10 is defined by the active connection between pin 41 and slot 42. An angle element 23, L-shaped in FIG. 5, is arranged between bearing block 10 and retaining element 2. Angle element 23 comprises a first section 30 as well as a second section 31. In the present embodiment, bearing block 10 comprises a back wall 29 as well as a base 28. First section 30 of angle element 23 is arranged between retaining element 2 and the base 28 of bearing block 10. Second section 31 runs essentially at a right angle to first section 30 and is arranged between clamping sleeve 3 of retaining element 2 and back wall 29 of bearing block 10. Bearing block 10 is seated on a slide part 12 so as to be able to rotate about a second axis of rotation 13. Second axis of rotation 13 is defined in the present embodiment by a clamp screw 39, the free end of which projects through a cutout 27 of base 28 and is terminated by a head part 26. First section 30 of angle element 23 comprises a slot-like cutout 24. Slot-like cutout 24 extends essentially parallel to the first axis of rotation 9 defining the displacement direction. First section 30 further comprises a first contact surface 40 facing base 28 and a second contact surface 25 facing head part 26. First contact surface 40 and second contact surface 25 run, at least in part, at an angle to one another along the displacement path. In the present example, second contact surface 25 is formed by the edge area of slot-like cutout 24. By displacing angle element 23 along the displacement path, first section 30 can be brought from a first position, in which first section 30 is not braced between base 28 and head part 26, into a second position, in which first section 30 is braced between base 28 and the head part, and thus bearing block 10 is pressed against slide part 12. By displacing angle element 23 along the displacement path, the degree of freedom defined by second axis of rotation 13 can thus be fixed in a given position or the fixation released.

Second section 31 of angle element 23 is flat on the surface facing back wall 29 of bearing block 10 and is conically shaped on the surface facing clamping sleeve 3. Clamping sleeve 3, moreover, has a contact section 38 that is likewise conically shaped. Clamping part 36 also has a conically shaped contact area 37. In the present embodiment, as shown from left to right in the representation of FIG. 5, contact area 37 is arranged adjacent to contact area 38, the latter in turn adjacent to second section 31 and the latter in turn adjacent to back wall 29. In contact area 38, clamping sleeve 3 comprises a concentrically arranged cutout 33. Moreover, second section 31 comprises a cutout 32 arranged concentrically to the conical profile and back wall 32 has a cutout 34. Rod-like section 35 of clamping part 36 penetrates cutouts 32, 33 and 34 and is joined to clamping wheel 15 by means of helical threads 43. By operating clamping wheel 15, rod-like section 35 can be screwed to a greater or lesser extent into helical threads 43 so that, depending on rotational sense of clamping wheel 15, the distance between contact surface 37 of clamping part 36 and clamping wheel 15 is reduced.

If clamping wheel 15 is turned such that the distance between contact area 37 and clamping wheel 15 is reduced, the following effect is produced (FIG. 5a shows the device in a fixed position of retractor arm 16 relative to slide part 12):

1. Clamp sleeve 3 and clamping part 36 are displaced relative to one another so that the cross section of cutout 7 is reduced and a retractor arm 16 inserted into cutout 7 is clamped by a friction fit between cutout 5 of clamping sleeve 3 and cutout 6 of clamping part 4. In this way, the two degrees of freedom defined by longitudinal axis 17 of retractor arm 16 relative to slide part 12, namely rotation about longitudinal axis 17 and displacement along longitudinal axis 17, are fixed.

2. First section 30 of angle element 23 is moved from left to right in FIG. 5 parallel to the displacement direction defined by first axis of rotation 9, whereby first section 30 is braced between head part 26 of clamp screw 39 and base 28 of bearing block 10 due to the contact surfaces 24 and 40 that run at an angle to one another, at least in a section. Thereby bearing block 10 is pressed against slide part 12, so that the degree of freedom of retractor arm 16 relative to slide part 12 defined by second axis of rotation 13 is fixed.

3. Moreover, contact area 37 of clamping part 36 is brought into contact with contact area 38 of clamping sleeve 3 due to the action of force on contact area 38, contact area 38 is brought into contact with first section 31 of angle element 23, and second section 31 of angle element 23 is pressed against back wall 29 of bearing block 10. The end result is that retaining element 2 is pressed against bearing block 10, so that the degree of freedom of retractor arm 16 relative to slide part 12 defined by axis of rotation 9 is fixed.

By rotational motion of clamping wheel 15 relative to clamping part 36, so that the distance between contact surface 37 and clamping wheel 15 is enlarged, there is the effect that the above-described fixing of the degrees of freedom is released.

The present embodiment also has a catch function for inserting retractor arm 16. To this end, a spring 44 that is braced between clamping wheel 15 and back wall 29 of bearing block 10 is provided. This has the effect that, in the unfixed rotational position of clamping wheel 15, clamping part 36 is displaced in the direction of first axis of rotation 9 relative to clamping sleeve 3, whereby a reduction of the cross section of cutout 7 is effected. If a retractor arm 16 is to be inserted into cutout 7 of retaining element 2, then clamping sleeve 3 and clamping part 36 must be displaced relative to one another against the force of spring 44 up to a position in which cutout 7 has a cross section is sufficiently large so as to accommodate retractor arm 16. If retractor arm 16 has been inserted into cutout 7, then retractor arm 16 is clamped by the elastic force of spring 44 between cutouts 5 and 6 of clamping sleeve 3 and clamping part 36. Thus, a retractor arm 16 can be inserted by a catch function into cutout 7 of retaining element 2. To prevent retractor arm 16 from slipping out of cutout 7, a catch bead 20 is preferably provided in the area of cutout 6 of clamping part 36.

FIG. 5b shows device 1 of the second embodiment with a partially inserted retractor arm 16 in a position in which retractor arm 16 is movable relative to the slide part.

Figure 6:
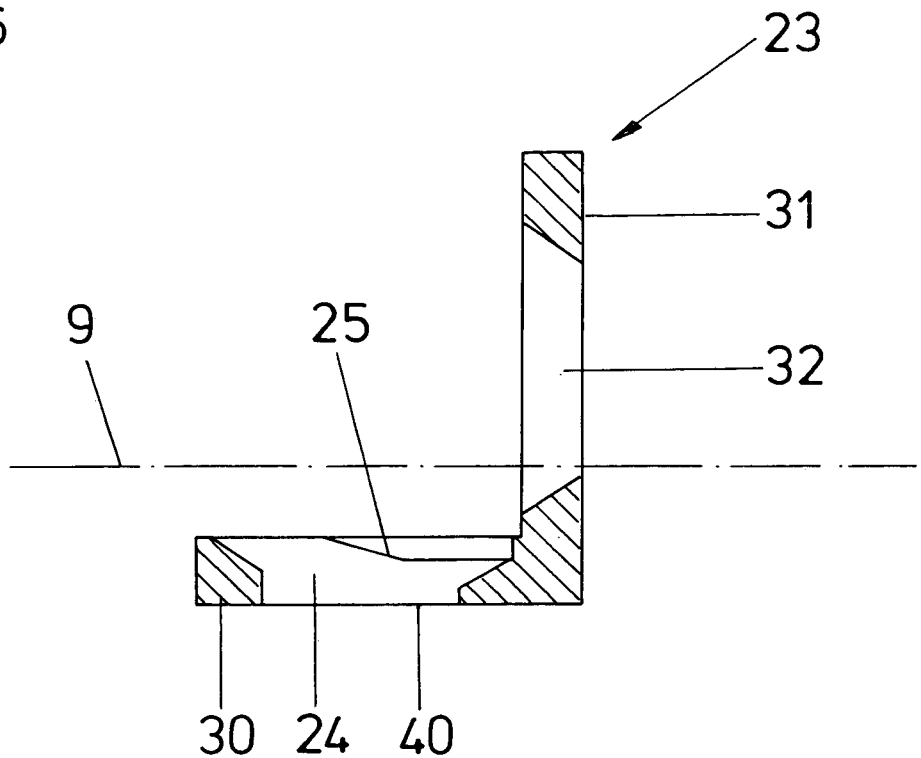
FIG. 6, an angle element according to the invention in keeping with the second embodiment, in cross section.

FIG. 6 shows a cross section of angle element 23 according to the invention. Angle element 23 comprises a first section 30 that runs essentially parallel to the displacement direction defined by first axis of rotation 9 as well as a second section 31 extending essentially perpendicular to first section 30. First section 30 provides a first contact surface 40 on its bottom side and a second contact surface 25 on its top side. Second contact surface 25 is arranged in the area of slot-like cutout 24. Slot-like cutout 24 extends essentially along the displacement direction. Moreover, second contact surface 25 runs at an angle to first contact surface 40, at least in sections. Second section 31 comprises a conical cutout 32.

Figure 7:
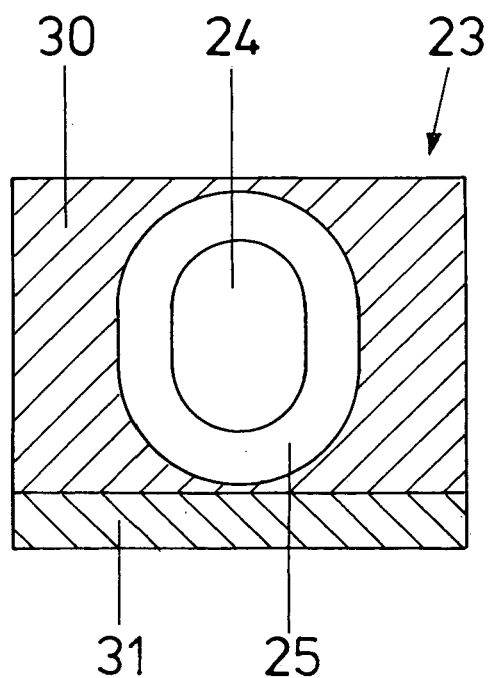
FIG. 7, the angle element in a plan view.

FIG. 7 shows an angle element 23 according to the invention from FIG. 6 in a plan view. One can recognize slot-like cutout 24, which is bordered by second contact surface 25.

LIST OF REFERENCE NUMBERS

1 Device for retracting tissue
2 Retaining element
3 Clamping sleeve
4 Clamping part
5 Cutout (clamping sleeve)
6 Cutout (clamping part)
7 Cutout (retaining element)
8 Shaft
9 First axis of rotation
10 Bearing block
11 Spring
12 Slide part
13 Second axis of rotation
14 Shaft
15 Clamping wheel
16 Retractor arm
17 Longitudinal axis
18 Blades
19 Slide rod
20 Catch bead
21 Slot (clamping sleeve)
22 Pin
23 Angle element
24 Slot-like cutout (angle)
25 Contact surface (slot-like cutout)
26 Head part (clamp screw)
27 Cutout (base)
28 Base (bearing block)
29 Back wall (bearing block)
30 First section (angle)
31 Second section (angle)
32 Cutout (second section)
33 Cutout (clamping sleeve)
34 Cutout (back wall)
35 Rod-like section (clamping part)
36 Clamping part
37 Conical section (clamping part)
38 Conical section (clamping sleeve)
39 Clamp screw
40 Contact surface
41 Pin (bearing block)
42 Slot (retaining element)
43 Helical threads
44 Spring

The invention claimed is:

1. Device (1) for retracting tissue or other parts of the body in surgical interventions, with a retaining element (2) having a throughgoing cutout (7) and with a blade (18) mounted on a retractor arm (16), wherein said retractor arm (16) is seated movably in said cutout (7), wherein said retaining element (2) comprises a clamping sleeve (3) and a clamping part (4, 36) movably guided in said clamping sleeve (3), where both said clamping sleeve (3) and said clamping part (4, 36) have a U-shaped throughgoing cutout (5, 6), wherein an overlap between said cutouts (5, 6) forms the throughgoing cutout (7) of the retaining element (2), said retaining element further comprising arrests for fixing said retractor arm (16), including springs (11), braced between clamping sleeve (3) and clamping part (4, 36), such that the cross section of the cutouts (5, 6) which is formed by said clamping sleeve (3) and clamping part (4, 36) has a smaller cross section than said retractor arm (16), said cutout (7) of said retaining element (2) is grooved in such a way that said retractor arm (16) can be inserted into the groove, orthogonal to a long extension of the groove and that said retractor arm (16) is fixed with respect to movements along said grooved cutout (7) after insertion into said grooved cutout (7) by said arrests.

2. Device (1) according to claim 1, characterized in that the device (1) comprises a slide part (12), where said retractor arm (16) is seated on said slide part (12) and is movable relative to the slide part (12) in at least four degrees of freedom, defined by at least three axes (9, 13, 17), wherein the at least three axes (9, 13, 17) intersect in one point.

3. Device according to claim 2, characterized in that retaining element (2) is arranged on slide part (12).

4. Device according to claim 2, characterized in that the axes of rotation (9, 13) that are not simultaneously axes of displacement (17) are at a right angle to one another.

5. Device according to claim 2, characterized in that a first degree of freedom is formed by infinitely variable rotatability about a first axis of rotation (9), a second degree of freedom by infinitely variable rotatability about a second axis of rotation (13), a third degree of freedom by infinitely variable rotatability about a third axis of rotation (17) and a fourth by infinitely variable movability along third axis of rotation (17).

6. Device according to claim 2, characterized in that slide part (12) can be displaced infinitely variably on a slide rod (19).

7. Device according to claim 1, characterized in that a clamping wheel (15) is provided which can be brought from a first position, in which retractor arm (16) is movable relative to slide part (12), into a second position, in which retractor arm (16) is fixed relative to slide part (12).

8. Device according to claim 1, characterized in that retractor arm (16) has a longitudinal axis and in that axis of rotation (17) is formed by its longitudinal axis (17).

9. Device according to claim 8, characterized in that retractor arm (16) can be rotated about its longitudinal axis (17) in cutout (7) of retaining element (2).

10. Device according to claim 1, characterized in that retractor arm (16) can be displaced along its longitudinal axis (17) in cutout (7) of retaining element (2).

11. Device according to claim 1, characterized in that retaining element (2) can be rotated relative to slide part (12) about first axis of rotation (9) and about second axis of rotation (13).

12. Device according to claim 1, characterized in that retaining element (2) has at least an approximately U- or V-shaped cross section.

13. Device according to claim 1, characterized in that retaining element (2) comprising clamping sleeve (3) and clamping part (4, 36), which is movably guided in clamping sleeve (3), the cross section of cutout (7) being modifiable by a displacement of clamping sleeve (3) relative to clamping part (4, 36).

14. Device according to claim 13, characterized in that clamping part (4, 36) and clamping sleeve (3) can be displaced relative to one another essentially parallel to first axis of rotation (9).

15. Device according to claim 13, characterized in that a catch bead (20) that projects into cutout (7) is formed on clamping part (4, 36) and/or on clamping sleeve (3), such that retractor arm (16) is surrounded in the inserted state by retaining element (2) over more than 180° in the circumferential direction.

16. Device according to claim 13, characterized in that a spring (11) is provided, braced between clamping sleeve (3) and clamping part (4, 36), such that the cross section of cutout (7) can be automatically reduced.

17. Device according to claim 13, characterized in that clamping wheel (15) is actively connected to clamping part (4, 36), the cross section of cutout (7) being modifiable by operation of clamping wheel (15).

18. Device according to claim 17, characterized in that clamping part (4, 36) has a rod like section (35) to which clamping wheel (15) is actively connected.

19. Device according to claim 18, characterized in that rod-like section (35) defines first axis of rotation (9).

20. Device according to claim 13, characterized in that contact area (37) of clamping part (36), back wall (29), and contact area (38) of clamping sleeve (3) are conically shaped and can be brought into contact with one another.

21. Device according to claim 13, characterized in that clamping sleeve (3) and clamping part (4, 36) can be rotated on bearing block (10) about axis of rotation (9).

22. Device according to claim 13, characterized in that clamping sleeve (3) comprises a slot (21) running essentially parallel to axis of rotation (9), in which a pin (22) is guided.

23. Device according to claim 1, characterized in that retaining element (2) surrounds retractor arm (16) in the inserted state by more than 180° in the circumferential direction.

24. Device according to claim 1, characterized in that retaining element (2) is arranged on slide part (12) by means of a bearing block (10), retaining element (2) being rotatable relative to bearing block (10) about first axis of rotation (9) and bearing block (10) being rotatable relative to slide part (12) about second axis of rotation (13).

25. Device according to claim 24, characterized in that on bearing block (10) a pin (41) is provided that is in active contact with a slot (42) in retaining element (2), such that rotational motion of retaining element (2) relative to bearing block (10) about first axis of rotation (9) is possible only within a specified angular range.

26. Device according to claim 24, characterized in that a friction fit contact between bearing block (10) and retaining element (2) can be produced and removed by operating clamping wheel (15).

27. Device according to claim 24, characterized in that bearing block (10) comprises a base (28) and a back wall (29) essentially perpendicular thereto.

28. Device according to claim 27, characterized in that slide part (12) and bearing block (10) are connected by means of a clamp screw (39) arranged on slide part (12), the free end of clamp screw (39) extending through a cutout (27) provided in base (28) of bearing block (10), and the free end being terminated by a head part (26).

29. Device according to claim 28, characterized in that clamp screw (39) defines second axis of rotation (13).

30. Device according to claim 28, characterized in that an angle element (23) is provided with a first section (30) arranged between base (28) and head part (26), first part (30) being movable relative to base (28) along a displacement path, and first section comprising a first contact surface (40) facing base (28) as well as a second contact surface (25) that faces head part (26) and runs, at least in a section at an angle to first contact surface (40), so that first section (30) can be brought by displacement along the displacement path from a first position, in which first section (30) is not braced between base (28) and head part (26), to a second position, in which first section (30) is braced between base (28) and head part (26) and bearing block (10) is pressed against slide part (12).

31. Device according to claim 30, characterized in that the displacement path runs parallel to first axis of rotation (9).

32. Device according to claim 30, characterized in that first section (30) comprises a slot-like cutout (24) extending in the displacement direction that is bordered by second contact surface (25).

33. Device according to claim 30, characterized in that angle element (23) can be displaced by means of clamping wheel (15).

34. Device according to claim 24, characterized in that angle element (23) comprises a second section (31), clamping part (36) a contact area (37), and clamping sleeve (3) a contact area (38), in that second section (31) and contact area (38) are arranged between back wall (29) and contact area (37), the two contact areas (37) and (38) being adjacent, and in that rod-like section (35) of clamping part (36) can be brought by displacement along the displacement path from a first position, in which second section (31), back wall (29) and the two contact surfaces (37, 38) are not in contact, into a second position, in which second section (31), back wall (29) and the two contact surfaces (37, 38) are in contact with one another.

35. Device according to claim 34, characterized in that the displacement path runs parallel to first axis of rotation (9).

36. Device according to claim 35, characterized in that second section (31) comprises a cutout (32), contact area (38) a cutout (33), and back wall (29) a cutout (34), which are penetrated by rod-like section (35) of clamping part (36).

37. Device according to claim 1, characterized in that clamping part (4) can be put into contact with bearing block (10).

38. Device (1) for retracting tissue or other parts of the body in surgical interventions, comprising:
- a clamping wheel (15);
- a slidepart (12);
- a bearing block (10) connected directly to said slide part (12) in such a way that said bearing block (10) is rotatable about a first axis, said first axis being orthogonal to the sliding direction of said slide part (12);
- a retaining element (2) with a throughgoing grooved cutout (7), wherein said retaining element (2) is rotatable about a second axis, said second axis being orthogonal to said first axis and intersecting said first axis at one point, wherein said cutout (7) is positioned orthogonal to said second axis and intersects said first and said second axis in the same point;
- a retractor arm (16) with a blade (18), said retractor arm (16) being seated movably in the direction of said cutout (7) and rotatable around a third axis defined by said throughgoing cutout (7), which is aligned orthogonal to said second axis and intersects said first axis and said second axis in the same point, after insertion of said retractor arm (16) into said cutout (7), and which can be inserted into a groove of said cutout (7) when said clamping wheel (15) is in a first position;
- wherein said clamping wheel (15) can be brought from said first position, in which said retractor arm (16) can be moved relative to the slide part in at least four degrees of freedom, three of which are defined by rotation about said first, second and third axis, into a second position, in which said retractor arm (16) is fixed relative to said slide part (12) in said at least four degrees of freedom.

* * * * *